(12) United States Patent
Fuselier (10) Patent No.: US 8,312,884 B2
(45) Date of Patent: Nov. 20, 2012

(54) INTRA-ORAL APNEA AND SNORING PREVENTION APPLIANCE

(76) Inventor: Brian D Fuselier, Maitland, FL (US)

(*) Notice: Subject to any disclaimer, the term of this patent is extended or adjusted under 35 U.S.C. 154(b) by 928 days.

(21) Appl. No.: 12/343,762

(22) Filed: Dec. 24, 2008

(65) Prior Publication Data

US 2010/0154802 A1   Jun. 24, 2010

(51) Int. Cl.
*A61F 5/56* (2006.01)
*A61F 5/37* (2006.01)
*A61C 5/14* (2006.01)
*A61C 3/00* (2006.01)
*A61C 9/00* (2006.01)
*A61C 19/04* (2006.01)
*A61C 5/00* (2006.01)

(52) U.S. Cl. ........ 128/848; 128/846; 128/857; 128/859; 128/861; 128/862; 433/6; 433/37; 433/41; 433/68; 433/140; 602/902

(58) Field of Classification Search .................. 128/846, 128/848, 857, 859, 861–862; 602/902; 433/6, 433/37, 41, 68–69, 140
See application file for complete search history.

(56) References Cited

U.S. PATENT DOCUMENTS

| | | | |
|---|---|---|---|
| 5,003,994 A | 4/1991 | Cook |
| 5,056,534 A | 10/1991 | Wright |
| 5,092,346 A | 3/1992 | Hays et al. |
| 5,117,816 A | 6/1992 | Shapiro et al. |
| 5,316,020 A | 5/1994 | Truffer |
| 5,409,017 A | 4/1995 | Lowe |
| 5,427,117 A | 6/1995 | Thornton |
| 5,537,994 A | 7/1996 | Thornton |

(Continued)

FOREIGN PATENT DOCUMENTS

GB    2415138 A    12/2005

(Continued)

OTHER PUBLICATIONS http://www.dentalartslab.com/tap-3-thornton-adjustable-positioner, *The Tap® 3 (Thornton Adjustable Positioner)*, Jun. 15, 2009, 6 pages, Dental Arts Laboratories, Inc., Peoria, Illinois.

(Continued)

*Primary Examiner* — Michael Brown
*Assistant Examiner* — Brandon L Jackson
(74) *Attorney, Agent, or Firm* — Buchanan Ingersoll & Rooney PC (57) ABSTRACT

An intra-oral device used for people that snore or have sleep apnea is designed to move a user's lower jaw forward relative to the user's immovable upper jaw and to prevent the user's mouth from inadvertently opening while sleeping. The device includes upper and lower appliances fitted to the user's respective upper and lower dental arches. The lower appliance possesses a partially embedded bracket. An adjustment element is integrated into the upper portion of the bracket. With the user's mouth closed and the upper and lower appliances positioned over the user's respective dental arches, the adjustment element is moved rearward by worm action into load bearing contact against the forward facing immovable vertical contact wall of the upper appliance. This action moves the lower appliance forward, and thus, the user's lower jaw with its anatomically attached tongue are also moved forward relative to the mouth which in turn opens the user's airway. Also, a forward facing horizontal shoulder positioned at the lowest portion of the vertical contact wall acts against the adjustment element to prevent the user's mouth from opening while sleeping.

30 Claims, 7 Drawing Sheets

U.S. PATENT DOCUMENTS

| | | | |
|---|---|---|---|
| 5,566,683 | A | 10/1996 | Thornton |
| 5,590,643 | A | 1/1997 | Flam |
| 5,720,302 | A | 2/1998 | Belfer |
| 5,755,219 | A | 5/1998 | Thornton |
| 5,829,441 | A | 11/1998 | Kidd et al. |
| 5,954,048 | A | 9/1999 | Thornton |
| 5,983,892 | A | 11/1999 | Thornton |
| 6,155,262 | A | 12/2000 | Thornton |
| 6,170,485 | B1 | 1/2001 | Orrico |
| 6,305,376 | B1 | 10/2001 | Thornton |
| 6,325,064 | B1 | 12/2001 | Thornton |
| 6,374,824 | B1 | 4/2002 | Thornton |
| 6,516,805 | B1 | 2/2003 | Thornton |
| 6,536,439 | B1 | 3/2003 | Palmisano |
| 6,845,774 | B2 | 1/2005 | Gaskell |
| 2003/0015198 | A1 | 1/2003 | Heeke |
| 2005/0150504 | A1 | 7/2005 | Heeke |
| 2005/0236003 | A1 | 10/2005 | Meader |
| 2006/0196512 | A1 | 9/2006 | Gaskell |
| 2006/0201520 | A1 | 9/2006 | Christensen |
| 2007/0079833 | A1 | 4/2007 | Lamberg |
| 2007/0163603 | A1 | 7/2007 | Sikora |
| 2007/0209666 | A1 | 9/2007 | Halstrom et al. |
| 2007/0292819 | A1 | 12/2007 | Scarberry |

FOREIGN PATENT DOCUMENTS

| | | |
|---|---|---|
| WO | WO 02/071989 A1 | 9/2002 |
| WO | WO 2006/070805 A1 | 7/2006 |
| WO | WO 2006/072147 A1 | 7/2006 |

OTHER PUBLICATIONS http://www.glidewell-lab.com/pdf/tech_sheets/tap_ts.pdf, *Clinical Techniques for Prescribing TAP Thornton Adjustable Positioner*, 2008, 2 pages, Glidewell Laboratories, Newport Beach, California.

http://www.quietsleep.com/oralappliancetherapy/oralappliancetherapy.cfm, Feb. 1, 2008, 73 pages, Quietsleep Creative, New York, New York.

http://www.sdsmithdmd.com/S1papnea.html, *Snoring/Sleep Apnea: Treatment of Snoring/Sleep Apnea with jaw Repositioning Intraoral Appliances*, Stephen David Smith, DMD, Sep. 2007, 7 pages, Elsevier-Saunders Publishers.

http://puresleep.com, *Pure Sleep*, Dr. Douglas Fenton, 2007, 2007, 23 pages, The Pure Sleep Company, Larkspur, California.

INTRA-ORAL APNEA AND SNORING PREVENTION APPLIANCE

TECHNICAL FIELD

The present application relates to an intra-oral appliance designed to move the lower jaw forward relative to the immovable upper jaw, for the treatment of sleep apnea or snoring, for instance.

BACKGROUND

Sleep apnea is a common sleep disorder in which a person experiences one or more pauses in breathing or shallow breaths during sleep. Sleep apnea is commonly associated with auto-retraction of the tongue resulting in a blockage of a patient's airway during sleep. This blockage of the airway by the tongue frequently leads to loud snoring or sleep apnea. Numerous oral devices have been used to attempt to solve this problem.

The basic design of these devices is to hold the movable lower jaw in a forward position while the user sleeps by utilizing a lever system designed to push against the immovable upper jaw. Since the tongue is attached to the front section of the lower jaw, repositioning the lower jaw forward acts to also reposition the tongue forward which in turn opens the patient's blocked airway allowing the patient to breathe freely while sleeping.

Examples of other devices which seek to prevent sleep apnea and/or snoring are shown in U.S. Pat. Nos. 5,427,117; 5,537,994; 5,566,683; 6,155,262; and 6,516,805, issued to Thornton. These devices share several common features, including upper and lower arches which cover the patient's teeth, and a downwardly extending post, extending from an inner side of the upper arch to contact the lower arch on an inner portion thereof. This contact holds the lower jaw at a forward position relative to the immovable upper jaw. One drawback of these designs is that the downwardly extending post or hook tends to obstruct the user's tongue as the post is positioned on the inside of the upper and lower arches, in the palatal region of the user. This obstruction of the user's tongue reduces the potential for the effectiveness of the appliance insofar as the idea is to pull the tongue forward and create a clear open space for the tongue.

Some of these devices also include an adjustment mechanism, to adjust the position of the lower arch relative to the upper arch. The adjustment mechanism presents another drawback to these devices; as such a mechanism is bulky. This bulkiness impedes the user's lips from closing properly which results in the user developing dry mouth and/or excessive drooling during sleep. This is counter-productive to normal sleep.

U.S. Pat. No. 6,155,262 issued to Thornton attempts to address the issue of the bulky adjustment mechanism by converting the device from an adjustable dental device to a non-adjustable dental device. While this action reduces the bulkiness to the lips, the device is no longer adjustable. The disadvantage to the non-adjustable design is that over time, some users' connective tissues that make up their jaw joints and their jaw musculature lengthen, making it necessary to reposition the user's lower jaw further forward. Therefore, in some cases, the non-adjustable appliance becomes progressively less effective over time by causing the user's connective tissues to lengthen and again allow the tongue to fully collapse into the user's airway.

Another patented oral device is disclosed U.S. Pat. No. 6,305,376 issued to Thornton. One drawback of this device is that its adjustment capability is also limited. In some cases, an end point to its adjustment capability is reached prior to meeting the needs of pulling the lower jaw far enough forward with respect to the upper jaw. This results in an ineffective device, in that the user's tongue remains collapsed in the user's airway. In other cases, this device becomes ineffective slowly over time due to the gradual lengthening of the connective tissue of the user's jaw joints and jaw musculature, respectively. This occurs due to the nightly repetitive forward positioning of the user's lower jaw. In these cases, the tongue slowly returns to once again block the user's airway.

SUMMARY

The present disclosure seeks to provide a sleep apnea and snoring prevention device without the drawbacks of the devices discussed above. Specifically, the present disclosure aims to provide an intra-oral sleep apnea and snoring prevention device that holds the movable lower jaw forward, keeps the user's mouth from opening while the user sleeps, does not encroach upon the tongue, allows for greater adjustment distance, allows for greater closure of the lips, and allows for greater sleep comfort.

In particular, the device includes an upper and a lower appliance which can be made of rigid thermoplastic acrylic to be fitted to a user's upper and lower dental arches, respectively. In a preferred embodiment, the lower appliance includes a bracket shaped like a lower case "h." The bracket is preferably made of medical grade stainless steel. The lower portion of the bracket is embedded in the lower appliance at the midline of the user's face. The upper portion of the bracket is un-embedded. The upper portion of the bracket extends upward from the rear section of the embedded lower portion of the bracket to end at a location above the mid lip plane. The upper portion of the bracket also lies between the user's upper lip and upper front teeth. An internally threaded loop or nut is solidly integrated into the distal end of the upper portion of the bracket. This nut is designed to receive a threaded adjustment element, such as a screw. The screw is preferably made of medical grade stainless steel and comes in lengths that vary from 5 mm to 20 mm, for example. With the user's mouth closed, and with the upper and lower appliances in place over their respective dental arches, the screw can be manually threaded into the nut by a tool that keys into the head of the screw. Rotation of the screw moves the screw horizontally and rearward into direct contact with the forward facing front outer portion or vertical contact wall of the upper appliance. Continued rotation in this one direction allows the screw to become load bearing against the vertical contact wall and thereby move the lower appliance forward with respect to the immovable upper appliance. The vertical contact wall may be reinforced using a medical grade stainless steel plate. This plate is useful to withstand excessive loading on the vertical contact wall from the forces generated through the screw.

The front portion of the immovable upper appliance includes a horizontal shoulder, preferably extending forward 2-3 mm and perpendicularly from the vertical contact wall. Rotation of the screw moves the screw in a rearward direction, with the respect to the mouth, until it abuts the forward facing vertical contact wall of the immovable upper appliance. The lower surface of the abutment end of the screw is designed to contact the forward facing vertical contact wall as well as the top surface of the immovable horizontal shoulder. This relationship between the top surface of the horizontal shoulder of the immovable upper appliance and the lower surface of the abutment end of the screw functions to prevent the abutment end of the screw from moving downward and thus prevents the user's mouth from opening while the user sleeps. If the user's mouth opens during sleep the lower jaw moves instantly rearward resulting in failure of the device.

In this embodiment, in order for the mouth to open, the user's lower jaw must come forward a predetermined distance to allow the abutment end of the screw to clear the immovable horizontal shoulder. When the lower jaw is held in a forward position an automatic rearward force, with respect to the mouth, is generated through the lower jaw by the lower jaw's musculature. This rearward force prevents any forward movement of the lower jaw while the user sleeps. Thus, the two appliances can not disengage while the user sleeps but can be easily disengaged when the user is awake.

The appliances are designed to be easily disengaged and removed by the user in the following ways. First, the user can consciously move his/her jaw forward enough to allow the abutment end of the screw to clear the immovable horizontal shoulder. Opening his/her mouth at this time will disengage the two appliances from each other. Second, the user holds warm water in his/her mouth for 20-25 seconds. The warmth of the water transfers to the thermoplastic acrylic making the appliances soft. Third, the user positions his/her thumbs onto the outer back lower edge of the lower appliance and applies an upward force with the thumbs. This will remove the lower appliance. Fourth, the upper appliance is removed by the user positioning his/her index fingers onto the outer back edge of the upper appliance then applies a downward force. This will remove the upper appliance.

Preferably, the upper and lower appliances are made of rigid thermoplastic acrylic; while the bracket, the adjustment element, and the reinforcement plate are preferably made of medical grade stainless steel.

BRIEF DESCRIPTION OF THE DRAWINGS

The objects and advantages of the disclosed device will become more apparent through the detailed description of the preferred embodiments in connection with the brief description of the drawings below.

DETAILED DESCRIPTION OF THE PREFERRED EMBODIMENTS

The subject matter here pertains to an intra-oral sleep apnea or snoring prevention device. The device as shown in FIGS. 1-7 comprises an upper appliance 110, a lower appliance 112, a bracket 114A-B, an adjustment element 118B, a vertical contact wall 110B on the front section of the upper appliance 110, and a horizontal ledge 110A also on the front section of the upper appliance 110. The upper and lower appliances fit over the user's respective upper and lower dental arches.

Figure 1:
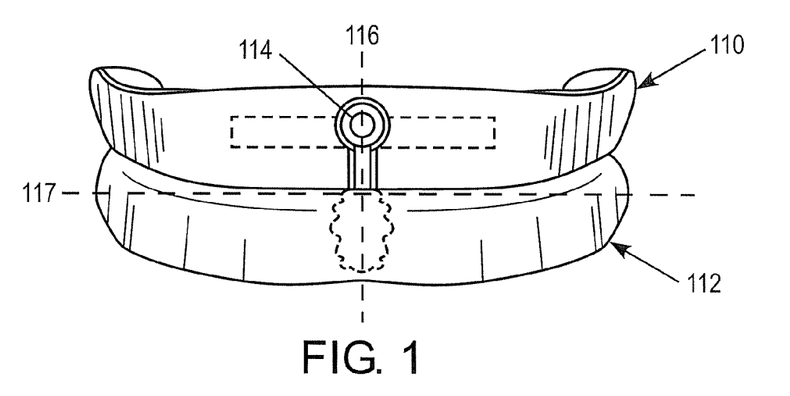
FIG. 1 illustrates a front view of the upper and lower appliances of the device according to an embodiment of the present invention.
Figure 2:
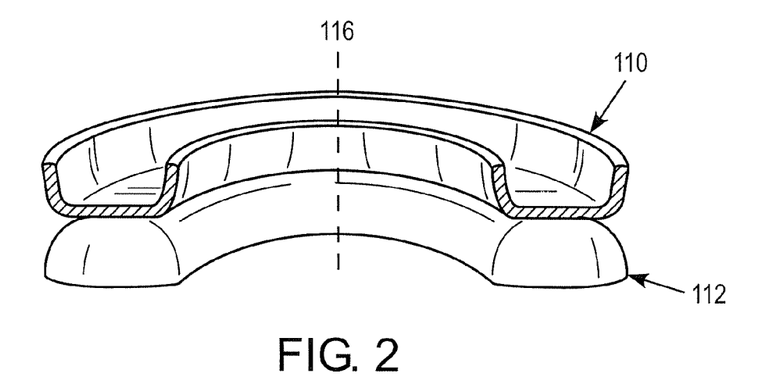
FIG. 2 illustrates a rear view of the upper and lower appliances of the device according to an embodiment of the present invention.
Figure 2A:
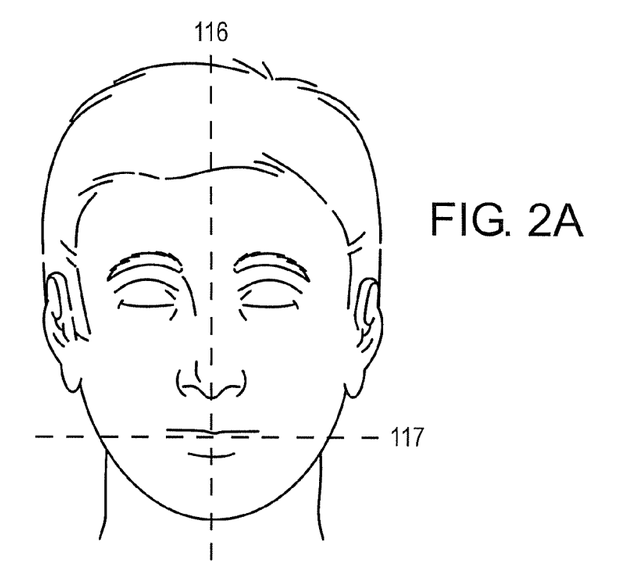
FIG. 2A illustrates the midline and the midlip line of the face.

As shown in FIGS. 1-4, the upper and lower appliances 110, 112 are formed in a substantially "U" shape, to match the dental arches of the user. The inner portion of the "U" shape defines the inside of each appliance 110, 112. The inside of the "U" shaped upper and lower appliances touches the palate and tongue, respectively, of the user. The outside portion of the "U" shaped appliances touches the user's lips or cheeks. Further, the open end of each "U" shaped appliance is the back portion of each appliance with respect to the user's mouth, while the closed end of each "U" shaped appliance is the front portion of each appliance 110, 112 with respect to the user's mouth. As shown in FIGS. 1, 2, and 2A, the midline 116 of the user's face is where both sides of the "U" shaped appliances join in the middle. The mid lip plane 117 is a plane defined by where the upper and lower lips of the user touch when the mouth is in a closed relaxed position.

The upper appliance 110 and lower appliance 112 are either custom fitted, or have various sizes to approximately fit the upper and lower dental arches of the user, respectively. In other words, the appliances 110, 112 can be sold in the form of standard sizes that approximate the fit of groups of potential users, semi-custom fit so that standard sizes are used, but further shaped to a more custom fit, or made to uniquely fit a user's mouth, using for instance, a molding process. The appliances 110, 112 may be adhered to the teeth, for example, by a frictional engagement with the teeth. The upper and lower appliances 110, 112 are preferably made of rigid thermoplastic acrylic and substantially match the surfaces of the user's upper and lower teeth, respectively. Alternatively, the upper and lower appliances may also be made from nearly any other material suitable for prolonged mouth exposure while maintaining sufficient rigidity to counteract the forces generated through the appliances.

In one procedure to match the upper and lower appliances 110, 112 to the surfaces of the user's respective upper and lower teeth, an impression of the user's teeth is made. From this, a model of the user's teeth is fabricated. The soft uncured thermoplastic acrylic of the upper and lower appliances 110, 112 can then be formed around the model of the user's teeth and cured to create the finished rigid upper and lower appliances 110, 112.

Figure 5:
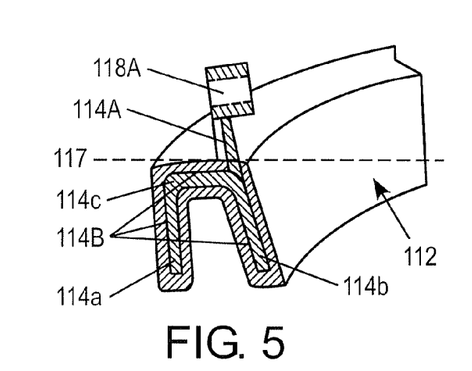
FIG. 5 illustrates a cross-section at the midline of the lower appliance taken along the line A-A according to the embodiment of FIG. 4.

In one embodiment, as shown in FIG. 5 the bracket 114A, B, and 118A is formed in the shape of a lower case "h." A lower portion 114B of the "h" is embedded into the lower appliance in such a manner that the bracket straddles the user's lower dental arch at the midline of the user's face. Alternatively, the lower part of the bracket 114B may be connected to the lower appliance 112 with other suitable fasteners, such as an adhesive or a mechanically interlocking relationship.

The lower portion 114B of the bracket 114 includes two legs 114a, 114b and a bridging portion 114c. As previously discussed, the lower portion 114B of the bracket is embedded into the lower appliance 112 at the midline of the face. Each leg 114a, 114b extends substantially vertically, i.e., substantially parallel, to the respective front and back surfaces of the user's teeth. Leg 114a is embedded on the outside portion of the lower appliance 112 and the leg 114b is embedded on the inside portion of the lower appliance 112. The two legs 114a, 114b are connected by a bridging portion 114c, which can be either embedded or un-embedded. The two legs 114a, 114b and the bridging portion 114c of the bracket thus straddle the lower teeth at the midline of the user's face.

The upper portion 114A and 118A of the "h" bracket is un-embedded. In a preferred embodiment, the upper portion extends upward from leg 114b to end at a location above the mid lip plane 117 of the user as well as between the upper front lip and the upper front teeth. In a preferred embodiment the bracket is made of medical grade stainless steel. However, other suitable materials may also be used. Alternatively, the upper portion 114A may extend from a front section of the bracket, i.e., from leg 114a.

Figure 3:
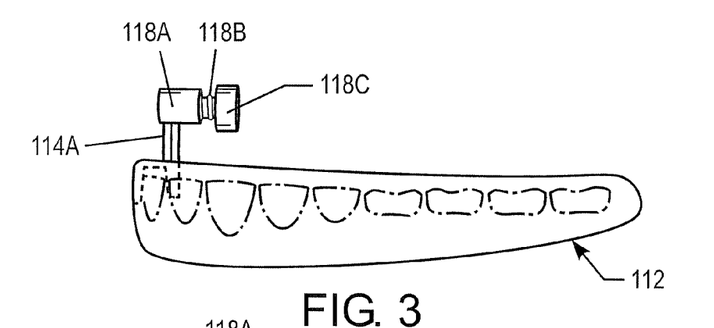
FIG. 3 illustrates a side view of the lower appliance and its adjustment element or screw according to the embodiment shown in FIG. 1.
Figure 4:
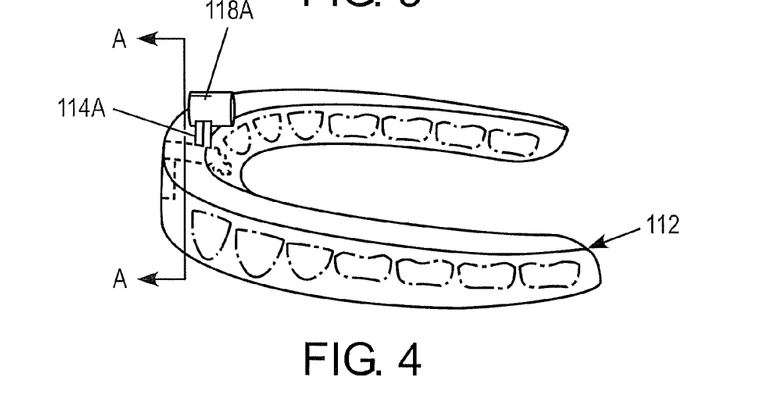
FIG. 4 illustrates an isometric view of the lower appliance without its adjustment element or screw present according to the embodiment of FIG. 1.

As shown in FIGS. 3 and 4, the upper part 114A of the "h" shaped bracket includes a solidly integrated internally threaded loop or nut 118A at its distal end. Preferably, the surface of the nut 118A facing the front of the user's mouth is flush with the surface of the upper part 114A facing the front of the user's mouth. This nut 118A is designed to be approximately 5 mm thick. However, this thickness may vary. In this embodiment, the nut is designed to receive an adjustment element 118B, such as a screw. The screw 118B comes in lengths that may vary from 5 to 20 mm. Further, the screw 118B can be adjusted by hand or by tool, or exclusively by tool. The nut 118A and the screw 118B are arranged in such a manner that the rotation of the screw 118B inside the nut 118A acts to move the screw 118B linearly forward or backward, relative to the mouth, depending on the direction of rotation. The interaction of the screw with the upper and lower appliances 110, 112, as is addressed in the following passages, provides forward movement of the movable lower jaw, with respect to the mouth, while maintaining a relatively small profile to the user's lips. Alternatively, the adjustment element can be a ratchet mechanism or a frictional clamping mechanism, for example.

The nut 118A and screw 118B are positioned between the user's upper lip and upper front teeth. Comfort of the user is maintained by shaving away any excess length of the screw that lies in front of the nut, relative to the mouth. Once the screw is adjusted properly the tongue no longer blocks the airway.

Figure 6:
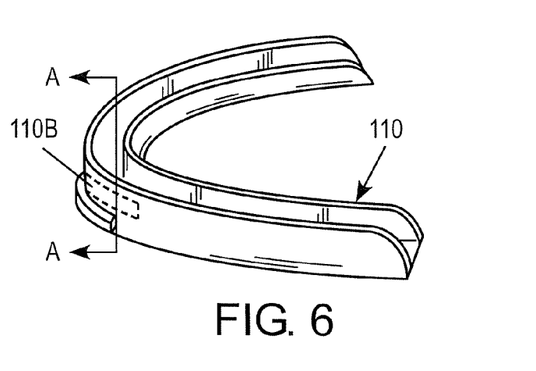
FIG. 6 illustrates an isometric view of the upper appliance according to the embodiment of FIG. 1.
Figure 7:
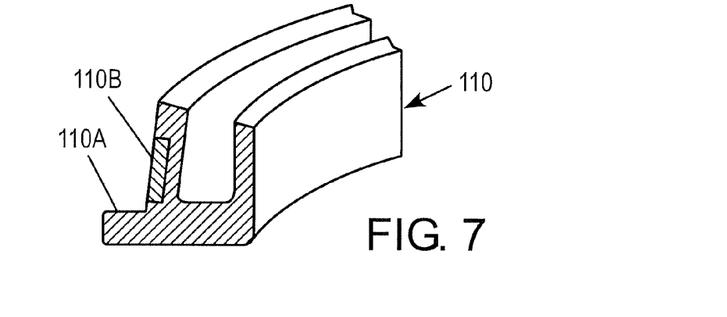
FIG. 7 illustrates a cross-section at the midline of the upper appliance taken along the line A-A in the embodiment of FIG. 6.

As shown in FIGS. 6 and 7, the outer, front part of the upper appliance 110 includes a vertical contact wall 110B. The vertical contact wall may be formed integrally with the upper appliance 110. This wall may also be reinforced using a medical grade plate of stainless steel or other suitable material. Nearly any durable material that can withstand the forces generated through the appliances, as well as continued abrasion and exist compatibly in the mouth for extended periods is suitable. For instance, the vertical contact wall 110B may be formed from materials including, without limitations, platinum, tungsten, titanium, hard acrylics, composites, and ceramics. The reinforcement may either be embedded in the upper appliance 110 or attached to the upper appliance 110 by suitable means, such as an adhesive. This reinforcement is useful as shown in FIG. 8 to counteract against the excessive forces generated through it by the interaction of the abutment end of the adjustment element 118C.

As shown in FIG. 6 the vertical contact wall 110B preferably extends from the midline 116 of the face to approximately 14 mm in each lateral direction and covers the vertical distance of the user's front teeth. However, the extent of the vertical contact wall in each lateral direction may vary depending on the potential lateral movement of the user's lower jaw.

In a preferred embodiment, as shown in FIG. 7, a horizontal shoulder 110A is formed at the front section of the upper appliance 110. This horizontal shoulder preferably extends 2-3 mm forward, with respect to the mouth, and perpendicular, with respect to the vertical contact wall 110B. Additionally, the horizontal shoulder 110A is an integrated part of the vertical contact wall 110B. Preferably, the horizontal shoulder 110A is made of the same rigid thermoplastic acrylic as the upper appliance 110. The horizontal shoulder 110A may also be made of a different material than the upper appliance 110, such as metal or other resistant material, and affixed to the upper appliance 110 by a suitable attachment device, for example, an adhesive.

Figure 8:
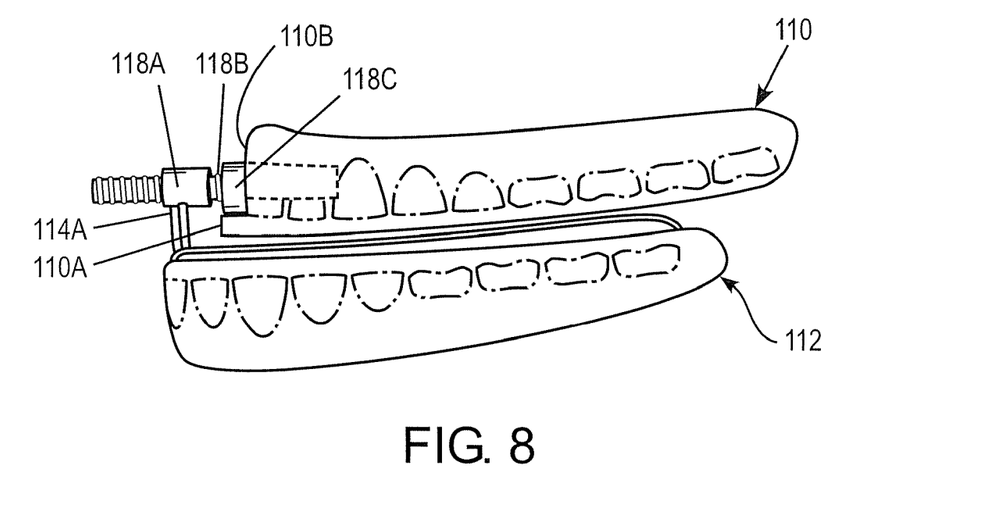
FIG. 8 illustrates a side view of the device where the lower appliance is in a forward position.

In operation, the disclosed intra-oral device as shown in FIG. 8 functions to reposition the user's movable lower jaw forward by utilizing a worm action against the immovable upper jaw. This device can be used for instance, in the treatment of sleep apnea and/or snoring. The device holds the user's lower jaw continuously forward, with respect to the mouth, while keeping the user's mouth closed during sleep.

Figure 9:
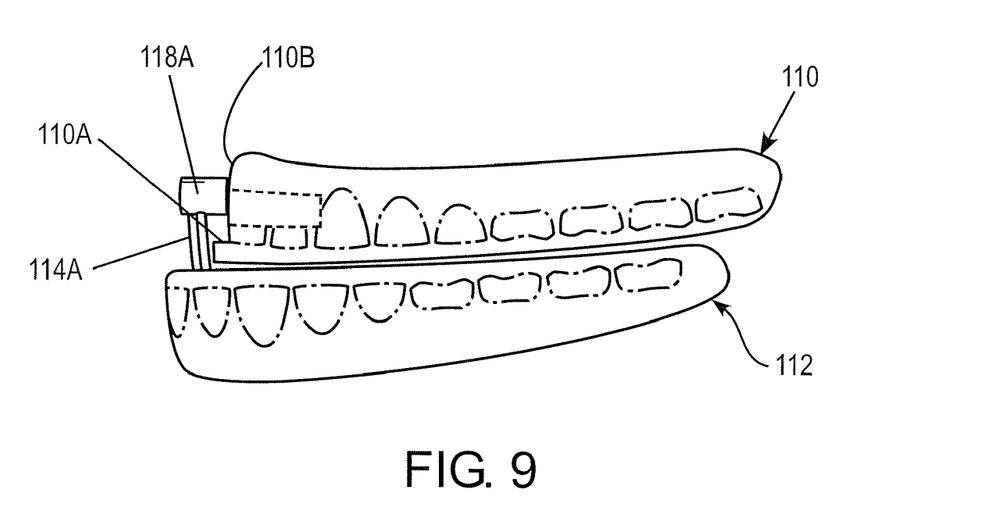
FIG. 9 illustrates a side view of the device where the lower appliance is adjusted to allow the lower jaw to position itself in a more rearward position

The user places the upper and lower appliances 110, 112 over their upper and lower dental arches, respectively. In order to position the user's lower jaw forward as shown in the embodiment of FIG. 8, the adjustment element, or screw 118B, is rotated in one direction within the nut 118A such that the screw head moves linearly rearward, with respect to the mouth. This linear rearward movement of the screw 118B results in the screw head or the abutment end of the screw 118C to come into contact with the forward facing vertical contact wall 110B of the immovable upper appliance 110. As the screw 118B is further rotated in the same direction, the force generated through the screw head moves the lower jaw forward, with respect to the mouth. Hence, since the lower appliance 112 is moved forward the user's lower jaw and tongue are also moved forward, with respect to the mouth. Rotating the screw 118B in the opposite direction or totally removing the screw as shown in FIG. 9 allows the lower appliance 112, and thus the lower jaw as well as the tongue, to move backward, with respect to the mouth. This allows for maximum adjustment for user's that can move their lower jaw forward only a small distance.

At one end of the screw is the screw head 118C. The screw may be manually threaded into the nut 118A of the bracket with the screw head facing toward the front of the mouth. The screw 118B can be rotated by a tool designed to key into the screw head 118C. The user can also reverse the orientation of the screw as shown in FIG. 8 such that the screw head is facing towards the back of the mouth. When the screw is in this reverse orientation the lower appliance 112 is removed to allow the screw 118B to be adjusted by the tool. This allows the head 118C of the screw to come into contact with the vertical contact wall 110B of the upper appliance 110. Once the screw head 118C is adjusted to abut the front side of the vertical contact wall 110B, any threaded part of the screw 118B that extends forward beyond the front face of the solidly integrated nut 118A of the bracket can be shaved flush with the front face of the nut to maintain a comfortable profile for the user's lip, as shown in FIG. 3. A tight contact is formed between the interface of the threads of the nut 118A and the threads of the screw 118B such that the screw is prevented from auto-rotating or rotating by incidental contact.

Rotation of the screw 118B in one direction as shown in FIG. 8 moves the rearward facing side of the screw head 118C into contact with the immovable forward facing vertical contact wall 110B of the upper appliance 110. This relationship between the screw head and the vertical contact wall also results in the lower surface of the screw head 118C contacting the immovable top surface of the 2-3 mm horizontal acrylic shoulder 110A. This relationship between the lower surface of the screw head 118C and the top surface of the horizontal shoulder 110A prevents the user's mouth from opening while the user sleeps.

In order for the user's mouth to open the lower jaw must come forward a predetermined distance to allow the screw head 118C to clear the immovable horizontal shoulder 110A. In a preferred embodiment, the predetermined distance is 2-3 mm, which corresponds to the distance of the horizontal shoulder 110A which extends from the front of the immovable upper appliance 110. When the lower jaw is held forward an automatic rearward force, with respect to the mouth, is generated through the lower jaw by the user's jaw's musculature. This rearward force restricts any forward movement of the lower jaw while the user sleeps. Thus, the two appliances 110, 112 can only be disengaged by removing one or both of the appliances or by the user consciously moving the lower jaw forward after he/she is awake.

As illustrated in FIG. 9, the internally threaded loop or nut 118A extends from the rearward section of the upper portion 114A of the bracket creating a shoulder. This rearward extension of the nut 118A allows the lower surface of the rearward facing portion of the nut to come into contact with the top surface of the horizontal shoulder 110A. This prevents the user's mouth from inadvertently opening. This arrangement may be utilized by persons who are unable to extend their lower jaw forward enough to allow the screw head to be inserted. When used in this way, a threaded insert can be threaded into the nut 118A to fill in the opening in the nut 118A.

Figure 10:
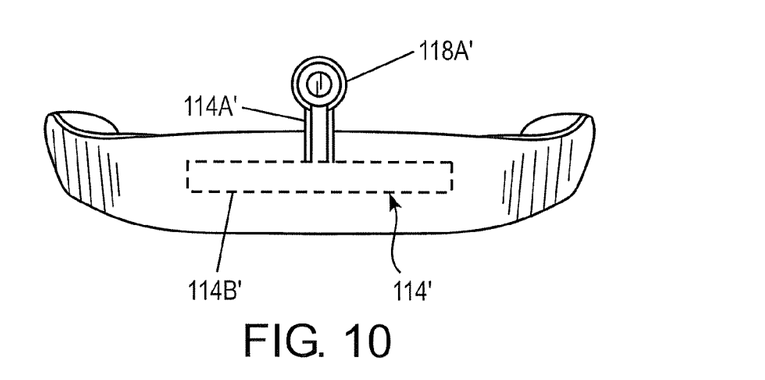
FIG. 10 illustrates the lower appliance of the device according to an alternative embodiment of the present invention.

In another alternative embodiment, as shown in FIG. 10, the bracket 114' can be of a different shape, for example, in the shape of an upside down upper case "T." In this embodiment, the lower portion of the "T" bracket 114B' is embedded at the midline of the face and extends laterally along the outer front part of the lower appliance. The upper portion of the upside down "T" bracket 114A' is un-embedded. A distal end of the upper portion of the upside down "T" bracket 114' includes a solidly integrated internally threaded loop or nut 118A'. This nut is designed to receive a threaded adjustment element or screw 118B, similar to the embodiment shown in FIGS. 1-4.

Figure 11A:
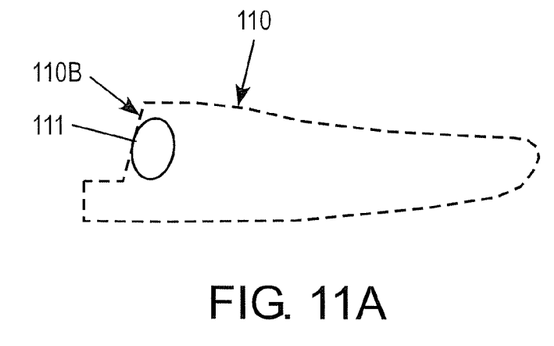
FIGS. 11A and 11B illustrate the upper appliance of the device according to an alternative embodiment of the present invention.
Figure 11B:
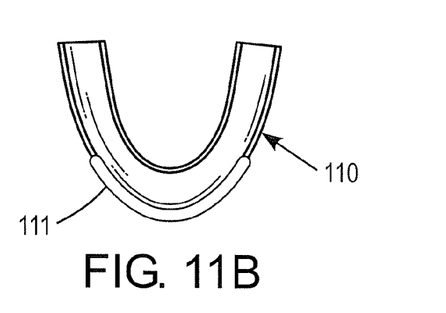

In another alternative embodiment, shown in FIGS. 11A and 11B, the reinforcement 111 of the vertical contact wall of the upper appliance 110 can be of a different shape, for example, in the shape of a tube. Such a tube extends from cuspid to cuspid horizontally, and can be circular, square, or any other suitable shape in cross-section, for example.

Figure 12:
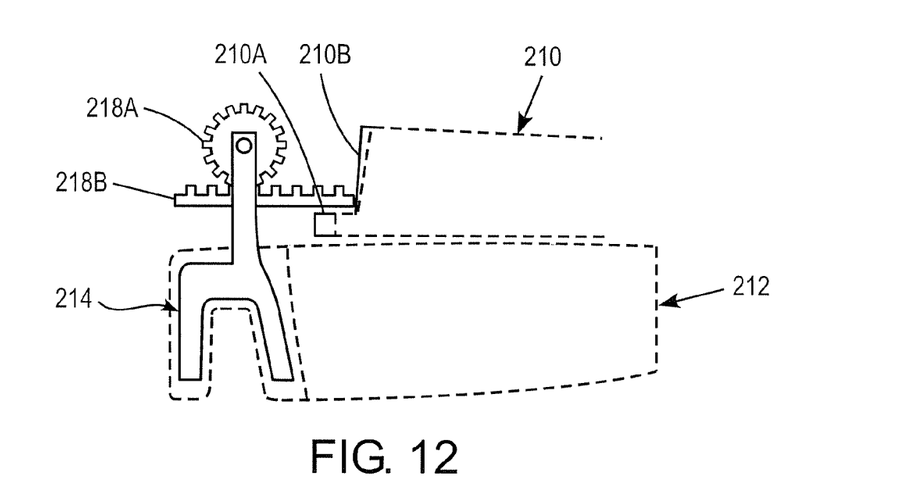
FIG. 12 illustrates the side view of the device according to yet another embodiment of the present invention.

FIG. 12 shows another alternative embodiment of the device. This embodiment includes an upper appliance 210, lower appliance 212, and bracket 214 as described above, including any combination of the aforementioned disclosed variants. However, this embodiment includes a different adjustment device 218A and 218B for adjusting the position of the lower appliance 212 relative to the upper appliance 210. Here, a driving gear 218A is positioned at the upper end of the upper portion 218A of the bracket 214. The driving gear 218A couples with a portion of a driven rod 218B which moves the rod linearly. Thus, upon rotation of the driving gear 218A in a first direction, the driving gear 218A will couple with the rod 218B and move the rod in a first axial direction to abut the vertical contact wall 210B of the upper appliance 210, this in turn will move the lower appliance 212 forward in relation to the immovable upper appliance 210.

Upon rotation of the driving gear 218A in a second direction, the driving gear 218A engages the driven rod 218B to move the driven rod 218B linearly in a second direction away from the vertical contact wall 210B of the upper appliance 210, and thus allow the lower appliance 212 to move backward relative to the immovable upper appliance 210. The driving gear 218A and driven rod 218B may be recognized in any suitable arrangement, including a worm gear, rack and pinion mechanism, or a ratcheting mechanism.

Similar to previous embodiments, the driven rod 218B may be supported by a horizontal shoulder 210A positioned on the front of the upper appliance 210 to prevent inadvertent opening of the mouth during sleep.

Figures 13, 14:
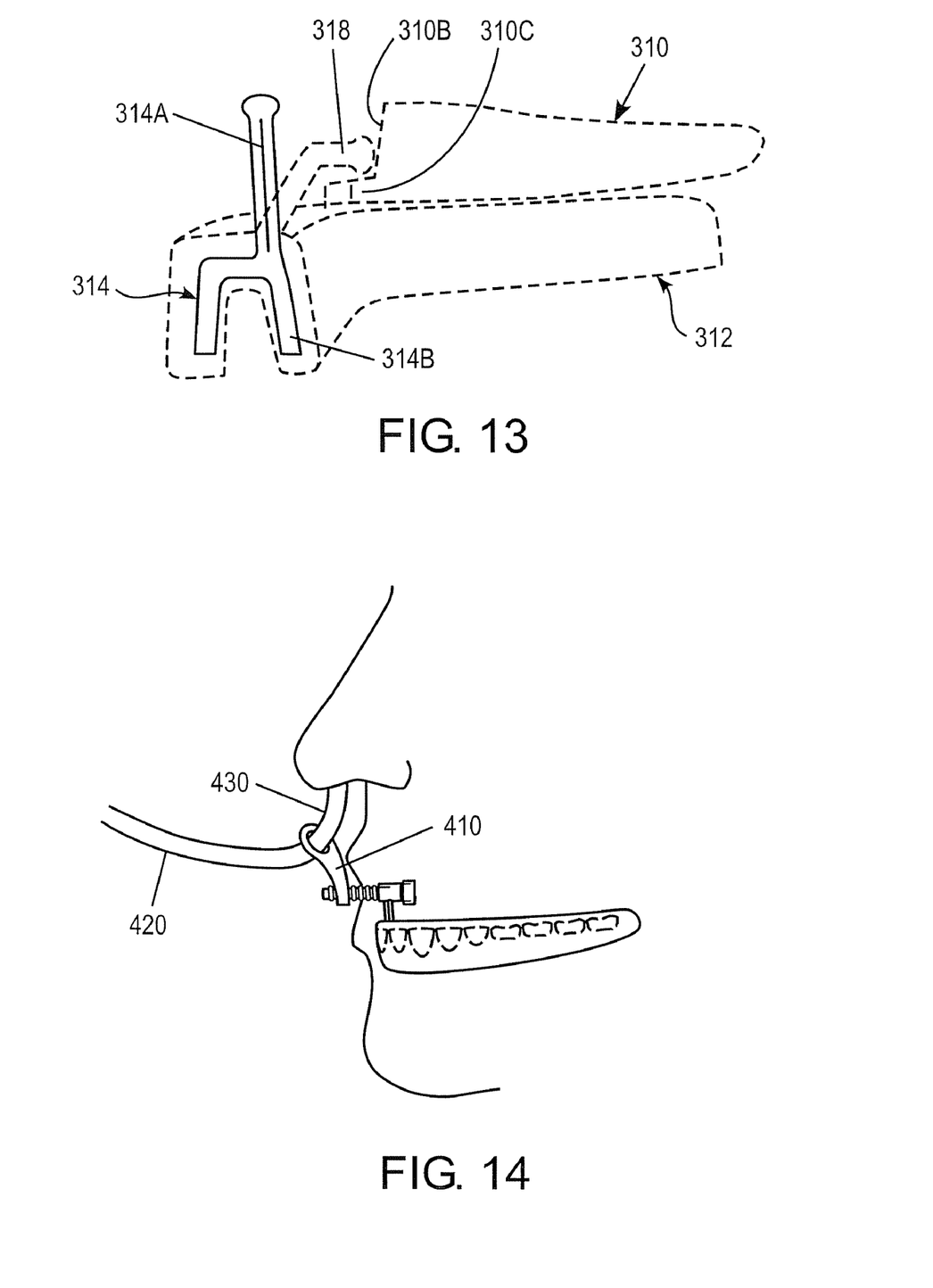
FIG. 13 illustrates another alternative embodiment of the present invention.
FIG. 14 illustrates another alternative embodiment of the present invention.

FIG. 13 shows another alternative embodiment. Here, the device includes upper and lower appliances 310, 312 as previously disclosed. The lower appliance 312 is equipped with a bracket 314 in any of the forms disclosed above. The bracket 314 can be made of any suitable metallic material that is deformable but is also able to withstand prolonged forces imparted from the user's lower jaw allowing the bracket to remain in its desired position. An example of this deformable metallic bracket is a ball clasp assembly which is presently used in dentistry to aid in retention of temporary partial removable bridges.

In this embodiment FIG. 13, an adjustment element 318 is realized through the distal end of the upper portion 314A of the bracket 314. The upper portion 314A of the bracket 314, extends upward from the rear section of the lower portion 314B of the bracket 314. The lower portion of the bracket is embedded in the lower appliance 312. The upper portion of the bracket is plastically deformable such that it is set in a position which fixes the lower appliance 312 in a forward position relative to the immovable upper appliance 310.

In use, the upper part 314A of the bracket is bent to a desired position to act upon the upper appliance 310, such that the distal end of the upper part 314A of the bracket (i.e., the adjustment member) abuts the vertical contact wall 310B of the upper appliance 310, thereby fixing the position of the movable lower appliance 312 in a forward position relative to the immovable upper appliance 310. Similar to the other embodiments, the upper appliance 310 includes a 2-3 mm horizontal ledge 310C which is designed to contact a portion of the adjustment member 318 when the device is in use, thereby acting to prevent the user from inadvertently opening his/her mouth.

Any of the embodiments disclosed above may have additional brackets, screws or ball clasps assemblies symmetrically placed along the outer section of the lower appliance to interface with the forward facing upper appliance's vertical contact wall. For example, the addition of second, third, or fourth bracket/adjustment element assemblies is suitable.

Placement of multiple assemblies reduces the penetrating force generated through the abutment end of the screw or ball clasp into the vertical contact wall of the upper appliance as well as reduces the force being generated through the embedded bracket. This significantly enhances the use of this appliance for users with extremely powerful jaw musculature or more frequently user's with weakened front teeth or missing front teeth.

Further, FIG. 14 demonstrates that any of the embodiments above may include an attachment device 410 where a tube from a Continuous Positive Airway Pressure (CPAP) device may be secured. A CPAP device is another device used to treat sleep apnea by providing a constant flow of pressurized air to the airway of the user. CPAP also maintains the user's airway in an open position. The CPAP device supplies pressurized air through tube 420.

The CPAP tube 420 can be connected to an intra-oral device in a manner that allows the CPAP device and the intra-oral device to operate in conjunction with each other. In one embodiment, not shown, the tube is secured to the mouth via the adjustment element or screw in a manner that the shape of the tube can be flattened to fit between the user's lips unobtrusively. The tube 420 may be circular in cross-section but may also be oblong and even substantially rectilinear in cross-section at a point where it passes through the user's upper and lower lips and teeth. Alternatively, as shown in FIG. 14, a portion 430 of the tube may be redirected by this oral device into the user's nostrils or into the user's mouth and nostrils simultaneously. In the latter arrangement, not shown, the tube 420 may be connected to a mask, which is placed over the user's mouth and nose. The mask can be attached to the oral appliance, thereby allowing for a reduction of the tightness of the fastening straps or eliminating the fastening straps that go around the user's head.

One other advantage of the oral device securing the CPAP tube to the face is that some user's no longer need the standard fastening straps that go around the head. When straps only are used, in common CPAP devices, movement of the head while the user is asleep may dislodge the mask resulting in immediate failure of the CPAP device. Attaching the mask to the oral appliance allows the mask to stay in place even when the user unconsciously rolls over while sleeping. Also, the straps create a backward directed force to the lower jaw which in some cases results in the development of painful Temporomandibular Dysfunction (TMD) to the user. Thereby, reducing the tension of the fastening straps or totally eliminating the fastening straps allow this subgroup of users to use CPAP without TMD pain developing.

In another embodiment shown in FIGS. 15A-15G is a fixed device without any movable parts designed for incremental forward advancement of the lower jaw with respect to the mouth. In particular, this device includes an upper appliance 510 and a lower appliance 512 fitted to the user's upper and lower dental arches, respectively. The lower appliance 512 includes a partially embedded bracket 514A that is positioned in the midline of the lower appliance 512. In a preferred embodiment, the bracket 514A is made of medical grade stainless steel or titanium and possesses an un-embedded shaft which extends vertically upward approximately 3 mm directly above the inside leg 514C of the bracket 514A. The upper end of the shaft possesses a rearward facing shoulder 514D, with respect to the mouth. The shouldered shaft 514A of the lower appliance fits into the receiving platform 514B of the upper appliance.

The receiving platform 514B of the upper appliance may be made from medical grade stainless steel or titanium, and is embedded at the midline section of the upper appliance 510, directly beneath the upper incisors, in relation to the mouth. The receiving platform is shaped like a rectangular box with the longest portion of the receiving platform positioned from front to back with respect to the mouth. The back wall of the receiving platform, with respect to the mouth, may be positioned approximately 3 mm to the back of the incisal edges of the upper incisors. The front wall of the receiving platform may extend forward approximately 7 mm beyond the incisal edges of the upper incisors. The ceiling of this receiving platform is its upper most surface, with respect to the mouth. The floor of this receiving platform is made of crossbars and represents the lowest most surface of the receiving platform, with respect to the mouth.

Figure 15A:
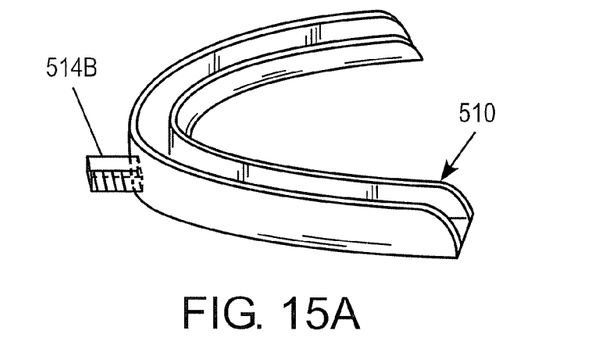
FIG. 15A through 15G illustrates another alternative embodiment of the present invention.
Figures 15B, 15C, 15D, 15E:
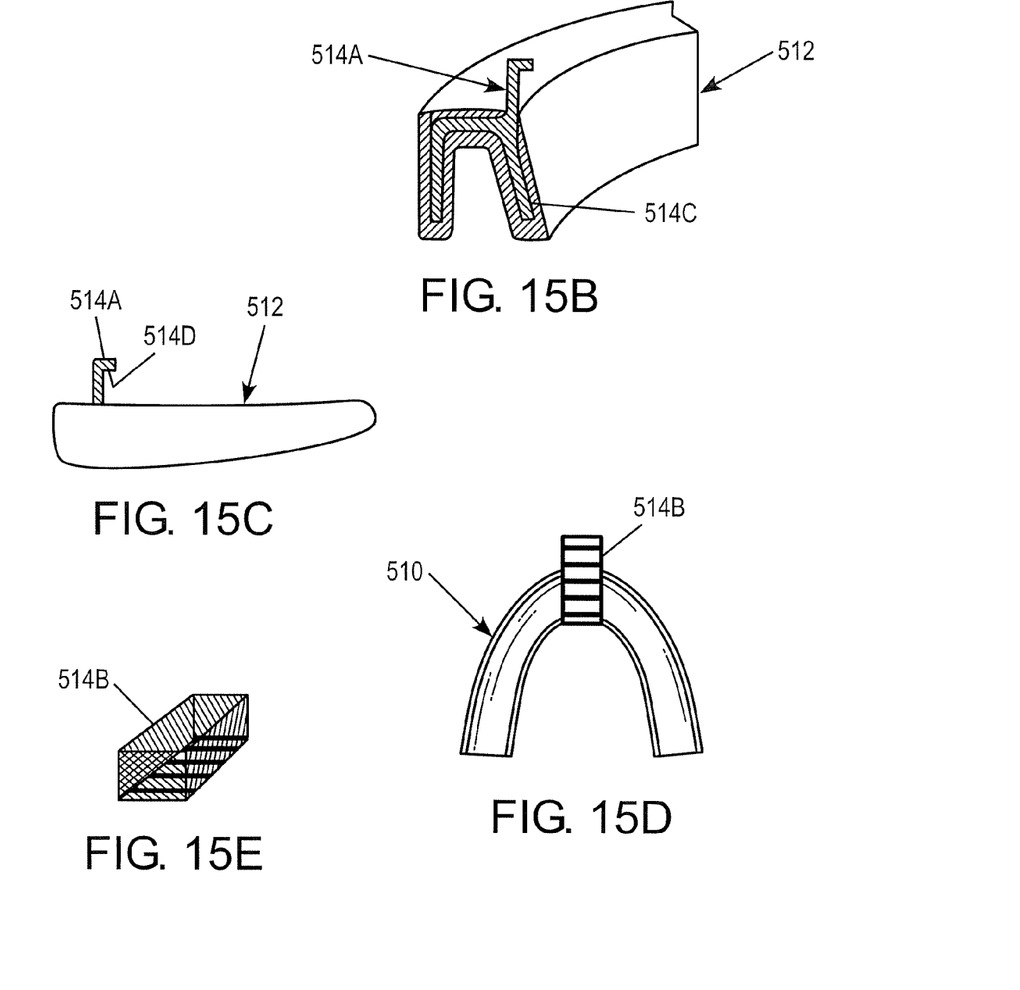
Figure 15F:
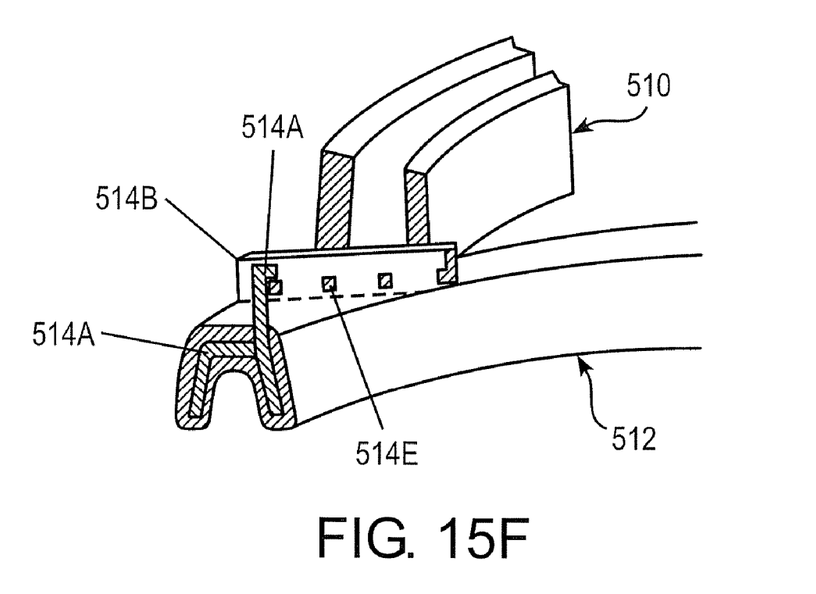
Figure 15G:
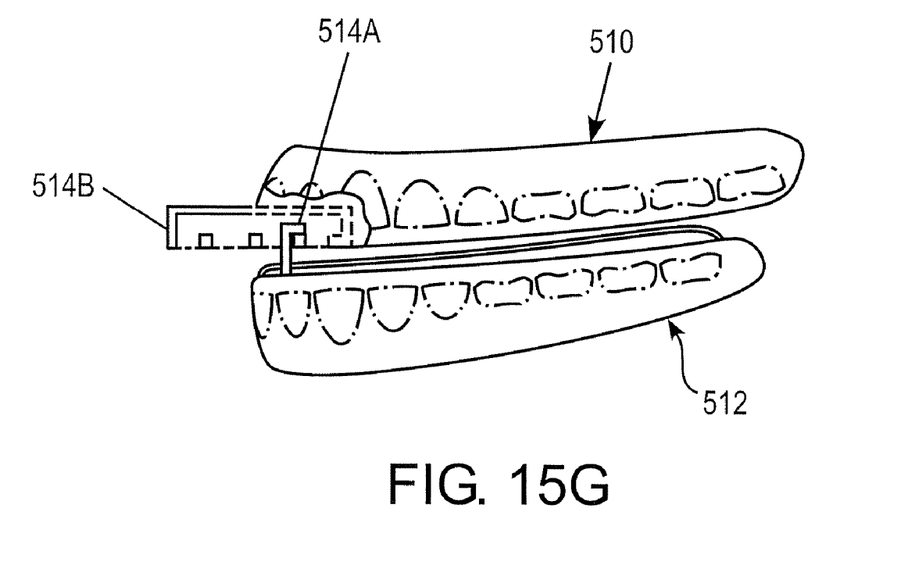

A channel is machined into the receiving platform 514B extending from front to back. Four crossbars as shown in FIGS. 15D and 15E are placed across the channel along its floor creating four spaces from front to back. In this preferred embodiment, the receiving platform from front to back, with respect to the mouth, is comprised of the front wall, the first space, the first crossbar, the second space, the second crossbar 514E, the third space, the third crossbar, the fourth space, the fourth crossbar, and the back wall. The four spaces created on the female portion of the receiving platform are designed to accept the male counterpart of the lower bracket 514A.

The user now advances and then closes his/her lower jaw. As the user closes his/her lower jaw the male end of the shouldered bracket 514A inserts itself into any one of the respective spaces on the receiving platform that would be best suitable for comfort and functionality for the user. Also, once the male portion 514A is seated in the female portion 514B, the shoulder of the male portion extending toward the rear of the mouth prevents uncoupling during sleep.

To uncouple the male portion 514A from the female portion 514B, the user must make a conscientious effort to move his/her lower jaw forward. This can only be performed when the user is consciously awake. Also, if necessary, the receiving platform can be removed from the upper acrylic appliance and repositioned further forward to accommodate patients that have hyper laxity in their jaw joints. Since the single greatest disadvantage of any mechanical design is failure of a moving part the advantage of this design is that it is the first device that allows for an incremental advancement of the lower jaw without any moving parts.

Further still, any of the above embodiments may be designed to create a flat biting surface on the upper appliance and a flat biting surface on the lower appliance. These two opposing flat biting surfaces are designed to create a balanced bite for the user when the user's mouth is tightly clenched.

Various changes and details may be made to embodiments of the invention described above without departing from the spirit of this invention. For example, the various embodiments and variations may be used together or in any combination.

The invention claimed is:
1. An intra-oral device comprising:
   an upper appliance configured to be fitted to an upper dental arch of a user;
   a lower appliance configured to be fitted to a lower dental arch of the user;
   a forward facing vertical contact wall and a horizontal shoulder positioned on an outer, front portion of the upper appliance;
   the lower appliance includes an "h" shaped bracket, a lower portion of the bracket is embedded into the lower appliance, and an un-embedded upward extending portion of the bracket has an adjustment element integrated into its distal end;
   wherein adjusting the adjustment element in one direction moves the adjustment element rearward, with respect to the user's mouth, to contact and become load bearing onto the forward facing vertical contact wall of the front portion of the upper appliance which moves the lower appliance forward with respect to the upper appliance, and adjustment of the adjustment element in an other direction moves the adjustment element away from the vertical contact wall and allows the lower appliance to move rearward with respect to the upper appliance; and in a state where the adjustment element is load bearing against the vertical contact wall, downward movement of the lower appliance relative to the upper appliance is restricted by contact between a lower rearward facing surface of the adjustment element and a forward facing horizontal shoulder of the upper appliance.

2. The intra-oral device of claim 1, wherein the lower portion of the h-shaped bracket is configured to straddle the teeth of the user, such that the lower portion of the bracket has an outside leg positioned on the outer, front side of the lower appliance, and an inside leg positioned at an inner side of the lower appliance, the two legs being joined together by a bridging element.

3. The intra oral device of claim 2, wherein the distal end of the upward extending portion of the bracket includes an internally threaded loop, and the adjustment element comprises a threaded adjustment device fitted into the internally threaded loop, such that rotation of the threaded adjustment device in a first rotational direction moves the threaded adjustment device linearly toward the upper appliance to become load bearing against the vertical contact wall, which in turn moves the lower appliance forward relative to the upper appliance, and rotation of the threaded adjustment device in a second, opposite, direction moves the threaded adjustment device away from the vertical contact wall and allows the lower appliance to move rearward relative to the upper appliance.

4. The intra-oral device of claim 3, wherein the threaded adjustment device is a screw.

5. The intra-oral device of claim 4, wherein the screw is made of medical grade stainless steel.

6. The intra-oral device of claim 4, wherein the screw has a length of 5-20 mm.

7. The intra-oral device of claim 3, wherein the bracket is made of medical grade stainless steel.

8. The intra-oral device of claim 3, wherein the upward extending portion of the bracket extends from the inside leg at the inner side of the lower appliance, the upward extending portion extends to a position adjacent to the outer, front portion of the upper appliance.

9. The intra-oral device of claim 8, wherein the upward extending portion extends to a position above a mid lip plane of the user.

10. The intra-oral device of claim 3, wherein the upper and lower appliances are formed of a shapeable material configured to take on the profile of the user's teeth.

11. The intra-oral device of claim 10, wherein the upper and lower appliances are made of acrylic.

12. The intra-oral device of claim 11, wherein the horizontal shoulder is made of acrylic.

13. The intra-oral device of claim 12, wherein the horizontal shoulder extends forward 2-3 mm relative to the mouth.

14. The intra-oral device of claim 13, wherein a lower surface of a rearward facing screw head of the screw as it abuts against the vertical contact wall of the upper appliance also comes into contact with the upper surface of the forward facing horizontal acrylic shoulder of the upper appliance; wherein downward movement of the lower appliance relative to the upper appliance is restricted, which in turn restricts any opening of the mouth of a user wearing the device.

15. The intra-oral device of claim 3, wherein the vertical contact wall is made of acrylic.

16. The intra-oral device of claim 15, wherein the vertical contact wall is reinforced.

17. The intra-oral device of claim 16, wherein the vertical contact wall is reinforced with a medical grade stainless steel plate.

18. The intra-oral device of claim 17, wherein the medical grade stainless steel plate is embedded in the acrylic.

19. The intra-oral device of claim 3, wherein the bracket is positioned on the lower appliance at a location corresponding to a midline of the user's face.

20. The intra-oral device of claim 1, wherein the bracket is made of medical grade stainless steel.

21. The intra-oral device of claim 1, wherein the vertical contact wall is reinforced.

22. The intra-oral device of claim 21, wherein the vertical contact wall is reinforced with a medical grade stainless steel plate.

23. The intra-oral device of claim 22, wherein the medical grade stainless steel plate is embedded in the vertical contact wall on the upper appliance.

24. The intra-oral device of claim 1, wherein the upper and lower appliances are formed of a shapeable material configured to take on the profile of the user's teeth.

25. The intra-oral device of claim 24, wherein the upper and lower appliances are formed from acrylic.

26. The intra-oral device of claim 1, wherein the adjustment element is adjustable with a tool.

27. The intra-oral device of claim 1, wherein the bracket is positioned on the lower appliance at a location corresponding to a midline of the user's face.

28. The intra-oral device of claim 1, wherein the upward extending portion of the bracket extends to a position above a mid lip plane of the user.

29. The intra-oral device of claim 1 wherein the device includes between 1 and 4 brackets equally spaced and symmetrically positioned along a front outer section of the lower appliance.

30. An intra-oral device comprising:
    an upper appliance configured to fit to an upper dental arch of a user; the upper appliance possessing an inner surface, an outer surface, a front portion, and a rear portion, wherein an area between the inner and outer surfaces of the upper appliance is adapted to receive the upper dental arch of the user;
    a lower appliance configured to fit to a lower dental arch of a user; the lower appliance possessing an inner surface, an outer surface, a front portion, and a rear portion, wherein an area between the inner and outer surfaces of the lower appliance is adapted to receive the lower dental arch of the user;
    at least one bracket having a lower portion embedded in the lower appliance and an upper un-embedded portion extending upward from the lower portion and terminating above the mid lip plane of the user, adjacent to the outer surface at the front portion of the upper appliance; and
    wherein the bracket is designed to receive an adjustment element positioned at the distal end of the upper portion of the bracket, the adjustment element being adjustable in a direction that allows it to travel towards the front surface of the upper appliance and to contact and apply such force onto the front surface of the upper appliance such that the lower appliance is moved forward relative to the upper appliance.

\* \* \* \* \*